United States Patent [19]

Olson

[11] Patent Number: 4,965,012

[45] Date of Patent: Oct. 23, 1990

[54] WATER INSOLUBLE ENCAPSULATED ENZYMES PROTECTED AGAINST DEACTIVATION BY HALOGEN BLEACHES

[76] Inventor: Keith E. Olson, 13952 Eveleth Court, Apple Valley, Minn. 55124

[21] Appl. No.: 316,599

[22] Filed: Feb. 27, 1989

Related U.S. Application Data

[63] Continuation of Ser. No. 40,191, Apr. 17, 1987, abandoned.

[51] Int. Cl.[5] .......................... C11D 3/38; C11D 7/42; C12N 11/14; D06L 3/16

[52] U.S. Cl. ................................. 252/174.12; 252/91; 252/99; 252/186.25; 252/186.35; 252/DIG. 12; 427/213; 427/214; 427/221; 435/188

[58] Field of Search ....................... 252/174.12, 174.13, 252/91, DIG. 12; 427/213, 214, 221; 435/188

[56] References Cited

U.S. PATENT DOCUMENTS

| | | | |
|---|---|---|---|
| 3,042,621 | 7/1962 | Kirschenbauer | 252/99 |
| 3,723,327 | 3/1973 | van Kampen | 252/110 |
| 3,893,954 | 7/1975 | Tivin | 252/548 |
| 4,421,664 | 12/1983 | Anderson | 252/94 |
| 4,552,679 | 11/1985 | Schobel | 252/90 |
| 4,707,287 | 11/1987 | Herdeman | 252/91 |
| 4,830,773 | 5/1989 | Olson | 252/174.13 |

*Primary Examiner*—A. Lionel Clingman
*Attorney, Agent, or Firm*—Merchant, Gould, Smith, Edell, Welter & Schmidt

[57] ABSTRACT

A composition capable of releasing active enzyme into an aqueous, active chlorine containing media which in a first aspect comprises an enzyme core encapsulated with an initial coating of a time-release substance, a first coating of a bleach-neutralizing substance and a second coating of a time-release substance.

In a second aspect, the composition comprises an enzyme encapsulated in a time-release substance designed to delay release of the enzyme in dissolution for a first-time delay, and a bleach-neutralizing substance, present as either a core material and/or a first coating on a diluent core, which is encapsulated in a time-release substance designed to delay release of the bleach-neutralizing substance into solution for a second-time delay; the first-time delay being longer than the second-time delay so that the bleach-neutralizing substance will be released and completely neutralize all active chlorine present in the solution before the enzyme is released.

In a third aspect, the composition comprises an enzyme core encapsulated with a time-release substance, a diluent core encapsulated with a first coating of a bleach-neutralizing substance and a second coating of a time-release substance, and a bleach-neutralizing substance core encapsulated with a time-release substance.

The invention further includes a cleaning composition which is particularly effective in warewashing which comprises one of the encapsulated enzyme-containing compositions described above, chlorine bleach, and at least one additional detergent component.

22 Claims, No Drawings

WATER INSOLUBLE ENCAPSULATED ENZYMES PROTECTED AGAINST DEACTIVATION BY HALOGEN BLEACHES

This is a continuation of application Ser. No. 07/040,191, filed Apr. 17, 1987 now abandoned.

FIELD OF THE INVENTION

The invention relates broadly to encapsulated enzymes and particularly to water soluble encapsulated enzymes which may be combined with a halogen bleach to form an effective bleach/enzyme cleaning composition.

BACKGROUND OF THE INVENTION

Enzymes are proteins synthesized by living organisms which can catalyze specific biochemical reactions such as the conversion of starch to sugar (amylase), the hydrolysis of fats to glycerol and fatty acids (lypase) and the hydrolytic breakdown of proteins (protease). It is commonly believed that enzymes are capable of catalyzing reactions only at a limited number of specific sites commonly referred to as "active sites".

Certain biological materials such as proteins, lipids and polysaccharides can be difficult to remove from substrates such as dishes, flatware and fabrics as such biological materials are substantially insoluble in traditional cleaning media. To increase the solubility and thereby effect removal of such biological materials, it is known to employ an enzyme in a cleaning media to catalytically assist in breaking down such materials into insoluble monomeric and/or oligomeric molecules. Certain types of enzymes such as amylase, lipase, and protease are known to be particularly useful for such purposes as they can effectively remove such materials from substrates without significantly degrading the substrate being cleaned.

Halogen bleaches are a well known group of chemical compounds having the ability to remove stains such as those caused by coffee and tea from a substrate. Halogen bleaches eliminate such stains by breaking down the large colored organic molecules which form such stains into smaller colorless molecules.

The cleaning actions of enzymes and halogen bleaches are complementary, each affecting different aspects of the soils typically found on dishes, flatware, and fabrics. Accordingly, a superior cleaning composition could be formed by employing both an enzyme and a halogen bleach in a single cleaning composition. However, while simple in theory such a combination has proven to be difficult to implement as halogen bleaches tend to instantly deactivate enzymes at concentrations as low as 1 part active halogen per one million parts cleaning media. While such deactivation of enzymes is not fully understood, it is believed that the halogen bleach affects either a change in the structure of the enzyme's active site or a change in the shape of the enzyme such that the enzyme's active site is no longer available as a reactor site.

Early attempts to combine a halogen bleach and an enzyme into a stable cleaning composition included the incorporation of a stabilizing amount of a polysaccharide into the cleaning composition, the incorporation of a stabilizing amount of a nonionic polymer into the cleaning composition, and coupling of the enzyme to an insoluble support. All of these early attempts met with limited success, encouraging research into other methods.

A slightly more successful attempt at combining a halogen bleach and an enzyme into a stable cleaning composition comprised encapsulation of the bleach in a time release coating. The time release coating delayed the release of the enzyme deactivating bleach for a time period sufficient to allow the enzyme to perform its cleaning function before it was deactivated. Unfortunately, this attempt also met with limited success as it proved virtually impossible to economically prevent premature release of an enzyme deactivating amount of the bleach.

A still slightly more successful attempt at combining a halogen bleach and an enzyme into a stable cleaning composition is disclosed in U.S. Pat. No. 4,421,664, which teaches that enzyme activity may be maintained in the presence of a halogen bleach by encapsulating the bleach in a time release coating and incorporating an amount of a reducing agent into the composition sufficient to substantially instantaneously reduce all prematurely released bleach. While this method has proven much more successful than earlier attempts, it has been discovered that in order for this method to work effectively it is necessary to employ an encapsulated bleach having an extremely high encapsulation efficiency which results in a prohibitively expensive composition.

Accordingly, a substantial need exists for an inexpensive and stable cleaning composition containing both an enzyme and a bleach wherein both the enzyme and the bleach may perform their desired cleaning function.

SUMMARY OF THE INVENTION

In a first aspect of my invention I have discovered a composition capable of releasing active enzyme into an aqueous, chlorine bleach-containing media, the composition comprising an enzyme core encapsulated with an inner coating of a bleach-neutralizing substance and an outer coating of a time-release substance. The encapsulated enzyme may further comprise an initial coating of a time-release substance between the enzyme and the bleach-neutralizing substance to ensure that all chlorine bleach present in the solution has been neutralized by the bleach-neutralizing substance before the enzyme is released.

In a second aspect of my invention I have discovered a composition capable of releasing active enzyme into an aqueous, chlorine bleach-containing media, the composition comprising an enzyme core encapsulated with a time-release substance designed to delay release of the enzyme into solution for a first-time delay, and a bleach-neutralizing substance encapsulated with a time-release substance designed to delay release of the bleach neutralizing substance into solution for a second-time delay; the first-time delay being longer than the second- time delay so that the bleach-neutralizing substance will be released and completely neutralize all chlorine bleach present in the solution before the enzyme is released. The bleach-neutralizing substance may be present either as a core material or as an inner coating material on a diluent core. Further, the enzyme may be encapsulated with an inner coating of bleach-neutralizing substance between the enzyme and the time-release substance.

In a third aspect of my invention I have discovered a composition capable of releasing active enzyme into an aqueous, chlorine bleach-containing media, the composition comprising an enzyme core encapsulated with a time-release substance, a diluent core encapsulated with an inner coating of a bleach-neutralizing substance and an outer coating of a time-release substance, and a bleach-neutralizing substance core encapsulated with a time-release substance. The enzyme core and the bleach-neutralizing substance core may be further encapsulated with an initial coating of a bleach-neutralizing substance between the core and the time-release substance. Still further, the enzyme core may be coated with the time-release substance so as to delay release of enzyme into solution for a first time delay, and the cores of diluent and bleach-neutralizing substance coated with the time-release substance so as to delay release of diluent and bleach-neutralizing substance into solution for a second time delay; the first time delay being longer than the second time delay so that all bleach-neutralizing substance present as either a core material or a coating material on a diluent core will be released and completely neutralize all chlorine bleach present in the solution before the enzyme is released.

In a fourth aspect of my invention I have discovered a cleaning composition particularly effective in warewashing which comprises at least one of the encapsulated enzyme containing compositions described above, a chlorine bleach, and at least one additional detergent component.

Commercially available enzymes typically contain a significant portion of an inert filler such as sodium sulfate, sodium chloride, or the like.

As utilized herein, unless otherwise indicated, "wt-% enzyme" refers to the active enzyme and any inert filler employed in combination with the enzyme. For example, the encapsulation of a mixture of 20 mg enzyme and 60 mg inert filler with an inner coating of 10 mg bleach-neutralizing substance and an outer coating of 10 mg time-release substance results in an encapsulated enzyme composition comprising 80 wt-% enzyme core.

As utilized herein, "bleach" refers to any chemical agent capable of removing the color from a substrate by oxidation.

As utilized herein, "active halogen" or "active chlorine" refers to the halogen or chlorine actually present in the compound having a valence of greater than $-1$.

For a detailed analysis of the meaning of "bleach", "active chlorine", and "available chlorine" see White, George, *Handbook of Chlorination,* 1972, pp. 188–190, which is herein incorporated by reference.

DETAILED DESCRIPTION OF THE INVENTION INCLUDING A BEST MODE

Encapsulated Enzyme

In a first aspect of my invention I have discovered a composition capable of releasing active enzyme into an aqueous, chlorine bleach containing media, the composition comprising an enzyme core encapsulated with an inner coating of a bleach-neutralizing substance and an outer coating of a time-release substance. The encapsulated enzyme may further comprise an initial coating of a time-release substance between the enzyme and the bleach-neutralizing substance to ensure that all chlorine bleach has been neutralized by the bleach-neutralizing substance before the enzyme is released.

Enzymes

Any enzyme capable of facilitating the removal of biological soil from a substrate without substantially damaging the substrate may be usefully employed in the present invention. Such enzymes includes proteases, lipases, amylases, and the like. The preferred enzyme or combination of enzymes depends upon the substrate to be cleaned and the types of soil to be removed. For reasons of ease of handling and ease of encapsulation, the enzyme is preferably powdered in form.

While commercially available enzymes typically contain a significant portion of an inert filler such as sodium sulfate, sodium chloride, or the like, I have found that the presence of such fillers does not affect the present invention.

Proteases (including peptidases) are those enzymes which attack and break down proteinaceous soils such as meat residue, gravy, and blood. Proteases are classified in EC class 3, subclass 3.4. I have found the EC class 3.4.4 peptide peptido-hydrolases such as subtilopeptidase A (EC 3.4.4.16) to be particularly effective in the cleaning composition of this invention. A suitable protease can be purchased from Novo Industries under the mark Esperase®.

Lipases are those enzymes which attack and break down fatty soils such as cooking oil, grease, and ice cream. Lipases also belong to EC class 3, but are placed in subclass 3.1. I have found the EC class 3.1.1 enzymes such as the glycerol ester hydrolases (EC 3.1.1.3) to be particularly effective in the cleaning composition of this invention. A suitable lipase can be purchased from Enzyme Development under the mark Lipase 30,000.

Amylases are those enzymes which can attack and break down starch, polysaccharide, and cellulosic soils such as potatoes, rice, oatmeal, and grass. Amylases also belong to EC class 3, but are placed in subclass 3.2. I have found the EC 3.2.1 glycoses hydrolases such as alpha-1, 4-glucan-4-glucanohydrolase (EC 3.2.1.1), and alpha-1, 4-glucan maltohydrolase (EC 3.2.1.2) to be particularly effective in the cleaning composition of this invention. A suitable amylase can be purchased from Novo Industries under the mark Termamyl®.

An in depth and detailed discussion of suitable enzymes can be found in U.S. Pat. No. 4,421,664, column 4, line 16 through column 6, line 24, which disclosure is herein incorporated by reference.

The encapsulated enzyme can comprise from a trace up to about 95 wt-%, based upon the total capsule, enzyme core. However, to allow sufficient bleach-neutralizing substance to be introduced into solution and to achieve an economical balance between encapsulation efficiency and amount of coating substance employed, the capsule preferably comprises about 50 to 80 wt-% enzyme.

Bleach-Neutralizing Substance

In the first aspect of my invention, surrounding and protectively encapsulating the enzyme core is an inner coating of a bleach-neutralizing substance which, when released into solution, reduces all active chlorine present in the solution to a form which will not deactivate the enzyme. The bleach-neutralizing substance should, of course, be a stable solid at room temperature and be compatible with the enzyme and all other components intended to be combined with the encapsulated enzyme. Further, the bleachneutralizing substance should not damage the substrate to be cleaned.

Any composition capable of reducing active chlorine to a form which will not deactivate an enzyme and which meets the criteria set forth above, can be usefully employed in the present invention. Suitable bleach-neutralizing substances include sulf-oxy acids and salts thereof, hydrogen peroxide producing compounds, sugars, and the like.

Sulf-oxy acids and the salts thereof are a well-known group of compounds which possess the ability to neutralize chlorine bleaches. For reasons of low cost, high performance, and ease of availability, the alkali metal and ammonium salts of sulf-oxy acids, such as ammonium sulfite ($(NH_4)_2SO_3$), sodium bisulfite ($Na_2SO_3$), sodium thiosulfite ($Na_2S_2O_3$), sodium metabisulfite ($Na_2S_2O_3$), potassium metabisulfite ($K_2S_2O_5$), lithium hydrosulfite ($Li_2S_2O_4$), and the like are preferred. Sulf-oxy acids are readily available from a number of suppliers including Allied Corporation under the mark Sulftech ®.

Because of their odorless and noncorrosive nature, the preferred chlorine bleach-neutralizing substances are those compounds capable of producing hydrogen peroxide when placed in solution. Such compounds include perborates, percarbonates, perphosphates, persulfates, and the like. These compounds are readily available from a number of suppliers including Interox Peroxid-Chemie GmbH and Dupont. For reasons of cost and ease of availability, the preferred hydrogen peroxide producing source is sodium perborate monohydrate available from Interox Peroxid-Chemie GmbH.

The encapsulated enzyme can comprise about 1 to 95 wt-%, based upon the total capsule, bleach-neutralizing substance. However, to achieve an economical balance between encapsulation efficiency and amount of coating substance employed and provide sufficient bleach-neutralizing substance to ensure complete neutralization of all active chlorine present in solution, the capsule preferably comprises about 10 to 60 wt-%, based upon the total capsule, bleach-neutralizing substance.

Time-Release Substance

In the first aspect of my invention, surrounding and protectively encapsulating the enzyme core and the first coating of bleach-neutralizing substance is an outer coating of a time-release substance. The time-release substance delays release of the bleach-neutralizing substance and the enzyme so that a bleach, used in combination with the capsule, can perform its cleansing function before it is deactivated by the bleach-neutralizing substance. The time-release substance should, of course, be compatible with the enzyme, the bleach-neutralizing substance, and all other components intended to be combined therewith. Further, the time-release substance should not damage the substance to be cleaned. Any material meeting these two criteria and capable of delaying the release of substantial amounts of the bleach-neutralizing substance for about 1 to 20 minutes, preferably about 2 to 6 minutes may be employed in the present invention.

Generally, the time-release substance will comprise a high molecular weight semisolid or solid fat, an inorganic solid, a natural or synthetic polymer, or the like. For reasons of excellent film formation, the preferred time-release substances are the natural and synthetic polymers. Suitable time-release polymers are well known in the art and include: cellulose derivatives such as sodium carboxymethyl cellulose, sodium hydroxyethyl cellulose, ethyl cellulose, hydroxypropyl cellulose, hydroxypropyl methyl cellulose, nitro cellulose, cellulose acetate phthalate, and hydroxypropyl methyl cellulose phthalate; gelatin; starch; proteins; fatty acids; waxes (including paraffin and microcrystalline waxes); polyacrylamide; polyacrylic acid; polyvinyl alcohol; polyethylene glycol, etc. The use of these and other similar time-release substances, including selection of an appropriate compound for a particular use, is well within the skill of one of ordinary skill in the art.

Because of its ability to suspend soils in solution in addition to its time-release characteristics, the preferred time-release substance is carboxymethyl cellulose and salts thereof. Suitable sodium carboxymethyl cellulose is available from a number of suppliers, including Hercules, Inc., under the mark CMC-CLT ®.

The encapsulated enzyme can comprise about 1–50 wt-%, based upon the total capsule, time-release substance. The preferred wt-% depends upon the particular substance employed and how long the bleach is to be allowed to function before it is deactivated by the bleach-neutralizing substance. For use in ware and fabric washing, I have found that about 1–20 wt-%, based upon the total capsule, time-release substance is typically satisfactory.

Initial Time-Release Substance

Optionally, the encapsulated enzyme can comprise an initial coating of a time-release substance between the enzyme core and the bleach-neutralizing substance to ensure that all of the active chlorine in solution has been neutralized by the bleach-neutralizing substance before the enzyme is released.

While I have found that excellent results may be obtained in the absence of this initial coating, it may be useful in some cases such as when an unstable enzyme is employed, a slow reacting reducing agent is employed or a small amount of reducing agent is employed. The initial coating of time-release substance can comprise any of the time-release substances previously described.

The amount of initial coating required to ensure that all active chlorine has been deactivated before the enzyme is released depends upon the amounts and type of bleach-neutralizing substance and initial coating material employed. However, I have found that about 0.5 to 5 wt-%, based upon the total capsule, initial coating material is typically sufficient to prevent premature release.

Combination of Encapsulated Enzyme and Encapsulated Bleach-Neutralizing Substance In a second aspect of my invention I have discovered a composition which comprises an enzyme encapsulated in a time-release substance designed to delay release of the enzyme into solution for a first-time delay, and a bleach-neutralizing substance encapsulated in a time-release substance designed to delay release of the bleach-neutralizing substance into solution for a second-time delay; the first-time delay being longer than the second-time delay so that the bleach-neutralizing substance will be released and completely neutralize all active chlorine present in the solution before the enzyme is released. The bleach-neutralizing substance may be present either as a core material or as a first coating on a diluent core. Further, the enzyme may be encapsulated with an inner coating of a bleach-neutralizing substance between the enzyme and the time-release substance. Still further, the enzyme may be initially encapsulated with a time-release substance.

Diluent

A diluent core may be employed as a carrier for bleach-neutralizing substance wherein the bleach-neutralizing substance is coated onto the diluent. This is particularly useful when the bleach-neutralizing substance does not readily form substantially uniform granules. The use of a diluent core allows both enzyme and diluent to be simultaneously coated with bleach-neutralizing substance, thereby simplifying manufacture.

Suitable diluents include sodium sulfate, sodium chloride, etc.

The enzymes, chlorine bleach-neutralizing substances, time-release substances, and chlorine bleaches described previously with respect to the first aspect are all equally well suited for use in this aspect. The time-release substance employed to coat the enzyme and the bleach-neutralizing substance may be the same or different. For ease of manufacturing, they are preferably the same.

This composition is particularly useful when the ratio of chlorine bleach-neutralizing substance to enzyme is so large that there simply is not sufficient enzyme particles upon which to attach sufficient chlorine bleach-neutralizing substance.

Generally, the time-release layers should be designed to prevent release of the bleach-neutralizing substance for at least about 1 minute, preferably about 2 to 6 minutes, and the enzyme should be protectively encapsulated for an additional 0.5–2 minutes after release of the chlorine bleach-neutralizing substance.

In this aspect the encapsulated enzyme particle can comprise from a trace up to about 95 wt-%, preferably about 30–80wt-% enzyme, about 0 to 10 wt-%, preferably about 0 to 5 wt-% initial coating of time-release substance, about 0 to 95 wt-%, preferably about 10 to 60 wt-%, bleach-neutralizing substance, and about 1–50 wt-%, preferably about 1–20 wt-% outer coating of time-release substance; and the encapsulated chlorine bleach-neutralizing substance can comprise from a trace up to about 95 wt-%, preferably 50 to 80 wt-% diluent core, from a trace up to about 95 wt-%, preferably about 50–80 wt-% chlorine bleach-neutralizing substance if employed as the core or about 15–40 wt-% chlorine bleach-neutralizing substance if employed as the first coat, and about 1–50 wt-%, preferably about 1–20 wt-% time-release substance.

Combination of Encapsulated Enzyme, Encapsulated Bleach-Neutralizing Substance and Encapsulated Diluent Having a Coating of Bleach-Neutralizing Substance In a third aspect of my invention I have discovered a composition which comprises an enzyme core encapsulated with a time-release substance, a diluent core encapsulated with an inner coating of a bleach-neutralizing substance and an outer coating of a time-release substance, and a bleach-neutralizing substance core encapsulated with a time-release substance. Further, the enzyme and the bleach-neutralizing substance cores may be encapsulated with an inner coating of a bleach-neutralizing substance between the core and the time-release substance. Still further, the time-release coating on the enzyme core may be designed to delay release of the enzyme into solution for a first time delay, and the time-release coating on the diluent core and the bleach-neutralizing substance core designed to delay release of the diluent and the bleach-neutralizing substance into solution for a second time delay wherein the first time delay is longer than the second time delay such that the bleach-neutralizing substance core and coatings will be released and completely neutralize all active chlorine present in the solution before the enzyme is released.

The enzymes, chlorine bleach-neutralizing substances, time-release substances, and chlorine bleaches described previously with respect to the first aspect are all equally well suited for use in this aspect. The time-release substance and bleach-neutralizing substance employed to coat the enzyme, the bleach-neutralizing substance and the diluent may be the same or different. For ease of manufacturing, they are preferably the same.

This composition is particularly useful when the ratio of chlorine bleach-neutralizing substance to enzyme is so large that there is insufficient enzyme particles upon which to attach sufficient chlorine bleach-neutralizing substance.

Generally, when encapsulating the enzyme, bleach-neutralizing substance and diluent to achieve early release of the bleach-neutralizing substance, the time-release layers should be designed to prevent release of bleach-neutralizing substance for at least about 1 minute, preferably about 2 to 6 minutes, and the enzyme should be protectively encapsulated for an additional 0.5–2 minutes after release of all of the bleach-neutralizing substance into solution.

In this aspect the encapsulated enzyme particle can comprise from a trace up to about 95 wt-%, preferably about 30–80 wt-% enzyme, about 0 to 10 wt-%, preferably about 0 to 5 wt-% initial coating of the time-release substance, about 0 to 95 wt-%, preferably about 10 to 60 wt-%, bleach-neutralizing substance, and about 1–50 wt-%, preferably about 1–20 wt-% outer coating of time-release substance; the encapsulated chlorine bleach-neutralizing substance can comprise about 50–80 wt-% chlorine bleach-neutralizing substance core, about 0–40 wt-% chlorine bleach-neutralizing substance coating, and about 1–50- wt-%, preferably about 1–20 wt-% time-release substance; and the encapsulated diluent can comprise about 30–80wt-% diluent core, 10–60 wt-% chlorine bleach-neutralizing substance and about 1–50 wt-%, preferably about 1–20 wt-%, time-release substance.

I have found a particularly easy and effective method of making encapsulated enzyme and bleach-neutralizing substance which achieves the desired order of release, the method comprising the steps of obtaining a diluent and a bleach-neutralizing substance having a granular size substantially the same as the enzyme granules, simultaneously coating the enzyme, diluent and bleach-neutralizing substance granules with a bleach-neutralizing substance, and then coating the once-coated granules with a time-release substance.

Cleaning Composition

In a fourth aspect of my invention, the compositions of the first, second and/or third aspects are combined with a chlorine bleach and at least one additional detergent component to form an effective cleaning composition. The chlorine bleach should be able to dissolve rapidly so that it may perform its cleaning function before the chlorine bleach-neutralizing substance is released. Many of the well-known chlorine bleaches are rapidly soluble and would be suitable for use in the invention.

Chlorine bleaches are a well-known group of compounds capable of releasing active chlorine ($Cl_2$) or hypochlorite (OCL—) ions into solution. Suitable chlorine bleaches include alkali metal dichloroiso- cyanurates, chlorinated trisodium phosphate, alkali metal and alkaline earth metal hypochlorites, monochloramine, dichloramine, nitrogen trichloride, [(mono-trichloro)-tetra-(mono-potassium dichloro)]pentaisocyanurate, 1,3-dichloro-5,5-dimethyl hydantoin, paratoluene sulfondi-chloroamide, trichlomelamine, N-chloromelamine, N-chlorosuccinimide, N,N'-dichloroazodicarbonamide, N-chloro acetyl urea, N,N'-dichlorobiuret, chlorinated dicyandiamide, trichlorocyanuric acid, dichlorogly- coluril, and the like. For reasons of excellent bleaching performance, the preferred bleaches are hydrated and anhydrous sodium dichlorisocyanurate and chlorinated trisodium phosphate. These bleaches are available from a number of commercial sources including Olin Corporation under the mark Clearon CDB-56 (sodium dichloroisocyanurate dihydrate) and Monsanto Industrial Chemical Co. under the mark ACL-56.

While the cleaning composition can comprise only chlorine bleach and encapsulated enzyme, for reasons of increased cleaning ability it preferably further comprises at least one additional detergent component such as a surfactant, a detergent filler, a detergent builder, a sequestrant, a chelating agent, etc.

Suitable organic surfactants include anionic, nonionic, amphalytic, zwitterionic, and mixtures thereof. While any compatible surfactant may be employed, surfactant types which are most widely used in detergent compositions include soaps (i.e., sodium or potassium salts) of fatty acids, rosin acids, and tall oil; alkylarenesulfonates; alkyl sulfates, including surfactants with both branched-chain and straight-chain hydrophobes, as well as primary and secondary sulfate groups; sulfates and sulfonates containing an intermediate linkage between the hydrophobic and hydrophilic groups, such as the fatty acylated methyl taurides and the sulfated fatty monoglycerides; long-chain acid esters of polyethylene glycol, particularly the tall oil ester; polyethylene glycol ethers of alkyl phenols; polyethylene glycol ethers of long-chain alcohols and mercaptans; fatty acyl diethanolamides; and block copolymers of ethylene oxide and propylene oxide.

Suitable detergent fillers, builders, sequestrants, and chelating agents include any of these well-recognized components whose functions include maintaining an alkaline pH, suspending particulate matter in solution, preventing redeposition of particulate matter, etc. A nonexhaustive list of such detergent fillers, builders, sequestrants and chelating agents includes condensed phosphates such as sodium tripolyphosphate, alkalis such as sodium carbonate, sodium metasilicate, and sodium hydroxide, fillers such as sodium sulfate, sodium bicarbonate and sodium chloride, soil suspending agents such as carboxymethylcellulose, and chelators such as ethylene diamine tetraacetic acid and polyacrylic acid.

The cleaning composition can comprise: about 0.1–1.5 wt-%, preferably about 0.5 to 1 wt-% available chlorine, about 0.3 to 20 wt-%, preferably about 1.5 to 15 wt-% encapsulated enzyme; an excess stoichiometric amount of an encapsulated bleach-neutralizing substance for the active chlorine, and about 0 to 99 wt-%, preferably about 55 to 95 wt-% additional detergent components. Preferably the cleaning composition contains up to 10 wt-% surfactant as an additional detergent component.

The amount of chlorine bleach-neutralizing substance employed must be sufficient to reduce all active chlorine present in the solution. Preferably the stoichiometric ratio of bleach-neutralizing substance to active chlorine is about 1:1 to 1.5:1 to ensure immediate deactivation of the active chlorine.

Method of Preparation

Preparation of the encapsulated enzyme and the encapsulated bleach-neutralizing substance can be accomplished in any of the several known encapsulating processes such as pan coating, roller coating, spray-congealing, etc. The preferred process is a fluidized bed process encapsulation.

Basically, encapsulation in a fluidized bed comprises the steps of (i) liquefying the coating materials by either melting the material or dissolving the material in a suitable solvent (preferably water);

(ii) fluidizing the particles to be encapsulated by placing the particles in a chamber and passing an oil flow therethrough;

(iii) coating the particles with the coating material by spraying the liquefied coating material onto the fluidized particles; and (iv) allowing the coated particles to cool and/or dry.

The cleaning composition may be prepared by simply blending all components together, being sure to minimize the possibility of damaging the capsules.

EXAMPLE I

Into a 32 liter container was placed 1.25 lbs. KLUCEL E, a hydroxypropyl cellulose purchased from Hercules, Inc., and 39.41 lbs. of soft water. The KLUCEL E and soft water were mixed until the KLUCEL E was completely dissolved. Into a fluidized bed was placed 23.75 lbs. TERMAMYL 60T, a powdered bacterial amylase purchased from Novo Industri a/s. The TERMAMYL 60T was fluidized in the bed at an air pressure of 40 psi, and the bed heated to 105° F. The entire amount of KLUCEL E solution was sprayed onto the fluidized TERMAMYL 60T granules through a Gustav Schlick Nozzle, Model 941. The fluidized bed was heated to 125° F. and the encapsulated TERMAMYL 60T dried therein for 1 minute. The capsules were cooled to 100° F. and removed from the bed. 24.5 lbs. of encapsulated TERMAMYL 60T was obtained.

Into the fluidized bed used above was placed 2.45 lbs. of the encapsulated TERMAMYL 60T and 27.86 lbs. granular sodium sulfate. Into the 32 liter container was placed 5.68 lbs. sodium perborate monohydrate purchased from Interox Peroxid-Chemie GmbH and 113 lbs. of soft water. The sodium perborate monohydrate and water were agitated until the sodium perborate monohydrate was completely dissolved.

The encapsulated TERMAMYL 60T and sodium sulfate were fluidized in the fluidized bed at an air pressure of 60 psi and the bed heated to between 140° to 168° F. The entire amount of sodium perborate monohydrate solution was sprayed onto the fluidized TERMAMYL 60T and sodium sulfate granules. The temperature of the fluidized bed was then adjusted to remain between 142° to 150° F., and the encapsulated granules allowed to dry. Into the 32 liter container was placed 2 lbs. KLUCEL E and 60 lbs. of soft water. The KLUCEL E and soft water were agitated until the KLUCEL E was completely dissolved. After the coating of sodium perborate monohydrate dried, the KLUCEL E solution was sprayed onto the once coated granules forming capsules with a first coating of sodium perborate monohydrate and a second coating of KLUCEL E. The fluidized bed was heated to 170° F. and the encapsulated granules dried therein for 2 minutes. The capsules were cooled to 100° F. and removed from the bed. Capsules retaining 90.4% of the original enzyme activity were obtained.

EXAMPLE II

Into a chlorine bleach solution of known concentration was placed an amount of the composition formed in Example I sufficient to create a 2% stoichiometric bleach-neutralizing excess of sodium perborate monohydrate. After allowing the outer coat of KLUCEL E, the coat of sodium perborate monohydrate, and the initial coat of KLUCEL E to dissolve, the solution was tested and found to contain 27.0% of the initial enzyme activity.

EXAMPLE III

Into a chlorine bleach solution of known concentration was placed an amount of the composition formed in Example I sufficient to create a 20% stoichiometric bleach-neutralizing excess of sodium perborate monohydrate. After allowing the outer coat of KLUCEL E, the coat of sodium perborate monohydrate, and the initial coat of KLUCEL E to dissolve, the solution was tested and found to contain 54.6% of the initial enzyme activity.

EXAMPLE IV

Into a 32 liter container was placed 1.5 lbs. sodium sulfate and 15 lbs. of soft water. The sodium sulfate and soft water were mixed until the sodium sulfate was completely dissolved.

Into a fluidized bed was placed 18 lbs. ESPERASE 4.0T, a powdered bacterial protease purchased from Novo Industri a/s. The ESPERASE 4.0T was fluidized in the fluidized bed at an atomization pressure of 40 psi and the bed heated to 125° F. The entire amount of sodium sulfate solution was heated to 120° F. and sprayed onto the fluidized ESPERASE 4.0T granules through a Gustav Schlick Nozzle, Model 941.

Into the 32 liter container was placed 4.67 lbs. sodium perborate monohydrate purchased from Interox and 93.48 lbs. of soft water. The sodium perborate monohydrate and water were agitated until the sodium perborate monohydrate was completely dissolved. The fluidized bed was heated to 130° F., the sodium perborate monohydrate solution maintained at less than 115° F., and the entire amount of sodium perborate monohydrate solution sprayed onto the once coated fluidized granules. Into the 32 liter container was placed 1.5 lbs. CMC-CLT, a sodium carboxymethyl cellulose purchased from Hercules, Inc., and 49.5 lbs. of soft water. The CMC-CLT and soft water were mixed until the CMC-CLT was completely dissolved. Finally, the CMC-CLT solution was maintained at less than 130° F. and the entire amount thereof sprayed onto the twice coated fluidized granules.

The fluidized bed was then heated to 130° F. and the thrice encapsulated granules dried therein for 1 minute, then cooled to 100° F. and removed from the bed.

EXAMPLE V

Into a beaker equipped with a laboratory stir bar and plate was placed 0.10 grams sodium dichloroisocyanurate dihydrate, 100.6 grams deionized water, and 0.34 grams encapsulated enzyme formed in Example IV. The mixture was vigorously agitated and complete neutralization of active chlorine found to take approximately 3 minutes. The resultant solution was found to have an enzyme activity of 2.28 knp units per gram of encapsulated enzyme representing a retention of 80% of the theoretical activity.

EXAMPLE VI

Into a 2 liter container was placed 470.5 grams sodium sulfate and 1600 grams soft water. The sodium sulfate and soft water were mixed until the sodium sulfate was completely dissolved.

Into a separate 1 liter container was placed 70.5 grams of a 3000 molecular weight polyacrylic acid and 211.5 grams soft water. The polyacrylic acid and soft water were mixed until the polyacrylic acid was completely dissolved.

Into a fluidized bed was placed 352.9 grams ESPERASE 4.0M, a powdered bacterial protease purchased from Novi Industri a/s. The ESPERASE 4.0M was fluidized in the bed and the bed heated to 80° F. The entire amount of sodium sulfate solution was heated to 84° F. and sprayed onto the fluidized ESPERASE 4.0M granules.

The fluidized bed was heated to 110° F. and the entire amount of the polyacrylic acid solution heated to 90° F. and sprayed onto the once coated granules. The fluidized bed was heated to 120° F. and the twice-coated granules dried therein, and then cooled to 100° F. and removed from the bed.

EXAMPLE VII

Into a beaker equipped with a laboratory stir plate, was placed 0.4 grams sodium dichloroisocyanurate dihydrate purchased from the FMC Corp. and 150 grams soft water heated to 140° F., and 1.0 gram of the encapsulated enzyme formed in Example VI. The mixture was vigorously agitated and found to effect complete neutralization of active chlorine. An EMPA 116 test cloth was placed in the solution and indicated enzyme activity.

The specification and Examples above are presented to aid in the complete nonlimiting understanding of the invention. Since many variations and embodiments of the invention can be made without departing from the spirit and scope of the invention, the invention resides in the claims hereinafter appended.

I claim:

1. An encapsulating enzyme composition capable of delivering active enzyme into a solution containing an active chlorine which comprises:

(a) an enzyme core comprising a protease, a lipase, an amylase, or mixtures thereof;

(b) a first encapsulating coating of a chlorine bleach-neutralizing substance comprising a sulf-oxy acid or salt thereof, a peroxide producing substance or a sugar; and (c) a second encapsulating coating of a time-release substance comprising a cellulose derivative.

2. The composition of claim 1 further comprising an initial encapsulating coating of a cellulose derivative between the enzyme core and the first coating.

3. The composition of claim 1 further comprising, in combination with the encapsulated enzyme, a encapsulated chlorine bleach-neutralizing which comprises:

(a) a core comprising a sulf-oxy acid or salt thereof, a peroxide producing substance or a sugar; and (b) an encapsulating coating of a cellulose derivative.

4. The composition of claim 1 further comprising, in combination with the encapsulated enzyme, a separately encapsulated diluent which comprises:

(a) a diluent core comprising inorganic salt;

(b) a first encapsulating coating of a sulf-oxy acid or salt thereof, a peroxide producing substance or a sugar; and (c) a second encapsulating coating of a cellulose derivative.

5. The composition of claim 4 wherein the diluent is an inorganic salt comprising sodium sulfate or sodium chloride.

6. The composition of claim 1 wherein the sulf-oxy acid or salt thereof comprises thiosulfite, metabisulfite, bisulfite, or salt thereof.

7. The composition of claim 1 wherein the peroxide producing substance is hydrogen peroxide, a perborate, persulfate, perphosphate, or percarbonate.

8. A cleaning composition comprising:

(a) an encapsulated enzyme which comprises:

(i) an enzyme core comprising a protease, a lipase, an amylase, or mixtures thereof;

(ii) a first encapsulating coating of a chlorine bleach-neutralizing substance comprising a sulf-oxy acid or salt thereof, a peroxide producing substance or a sugar; and (iii) a second encapsulating coating of a time-release substance comprising a cellulose derivative;

(b) a chlorine bleach, and (c) at least one additional detergent component selected from surfactants, detergent fillers, detergent builders, sequestrants, and chelating agents.

9. A cleaning composition comprising:

(a) an encapsulating enzyme which comprises:

(i) an enzyme core comprising a protease, a lipase, an amylase, or mixtures thereof;

(ii) a first encapsulating coating of a chlorine bleach-neutralizing substance comprising a sulf-oxy acid or salt thereof, a peroxide producing substance or a sugar; and (iii) a second encapsulating coating of a time-release substance comprising a cellulose derivative;

(b) an encapsulated diluent which comprises:

(i) a diluent core comprising an inorganic salt;

(ii) a first encapsulating coating of a sulf-oxy acid or salt thereof, a peroxide producing substance or a sugar;

(iii) a second encapsulating coating of a cellulose derivative;

(c) a chlorine bleach, and (d) at least one additional detergent component selected from surfactants, detergent fillers, detergent builders, sequestrants, and chelating agents.

10. A cleaning composition, comprising:

(a) about 0.3–20 wt-%, based upon the cleaning composition, encapsulated enzyme which comprises:

(i) about 1 to 95 wt-%, based upon the encapsulated enzyme, enzyme core comprising a protease, a lipase, an amylase, or mixtures thereof;

(ii) about 1–95 wt-%, based upon the encapsulated enzyme, first encapsulating coating of a chlorine bleach-neutralizing substance comprising a sulf-oxy acid or salt thereof, a peroxide producing substance or a sugar; and (iii) about 1–50 wt-%, based upon the encapsulated enzyme, second encapsulating coating of a time-release substance comprising a cellulose derivative;

(b) about 0.1–40 wt-% chlorine bleach; and (c) about 55–95 wt-%, based upon the cleaning composition, of at least one additional detergent component selected from the group consisting of detergent fillers, detergent builders, surfactants, sequestrants, and chelating agents.

11. A cleaning composition comprising:

(a) about 0.3–20 wt-%, based upon the cleaning composition, encapsulated enzyme which comprises:

(i) about 1 to 95 wt-%, based upon the encapsulated enzyme, enzyme core comprising a protease, a lipase, an enzyme, or mixtures thereof;

(ii) about 1–95 wt-% based upon the encapsulated enzyme, first encapsulating coating of a chlorine bleach-neutralizing substance comprising a sulf-oxy acid or salt thereof, a peroxide producing substance or a sugar; and (iii) about 1–50 wt-%, based upon the encapsulated enzyme, second encapsulating coating of a time-release substance comprising a cellulose derivative;

(b) at least a sufficient bleach neutralizing amount of an encapsulated diluent which comprises:

(i) about 1–95 wt-%, based upon the encapsulated diluent, of a diluent core comprising an inorganic salt;

(ii) about 1–95 wt-%, based upon the encapsulated diluent, first encapsulating coating of a sulf-oxy acid or salt thereof, a peroxide producing substance or a sugar; and (iii) about 1–50 wt-%, based upon the encapsulated diluent, second encapsulating coating of a cellulose derivative;

(c) about 0.1–40 wt-%, based upon the cleaning composition, chlorine bleach; and (d) about 55–95 wt-%, based upon the cleaning composition, additional detergent components selected from the group consisting of detergent fillers, detergent builders, surfactants, sequestrants, and chelating agents.

12. The cleaning composition of claim 9 wherein the hydrogen peroxide producing substance is hydrogen peroxide, a perborate, persulfate, perphosphate, or percarbonate.

13. The cleaning composition of claim 9 wherein the peroxide producing substance is hydrogen peroxide, a perborate, persulfate, perphosphate, or percarbonate.

14. An aqueous cleaning composition comprising, in an aqueous medium;

(a) an effective cleaning concentration of a rapidly soluble active chlorine bleach in the aqueous cleaning composition; and (b) an encapsulated enzyme comprising:

(i) an enzyme core comprising a protease, a lipase, an amylase, or mixtures thereof;

(ii) a first encapsulating coating of a chlorine bleach-neutralizing substance comprising a sulf-oxy acid or salt thereof, a peroxide producing substance or a sugar; and (iii) a second encapsulating coating of a time-release substance comprising a cellulose derivative, wherein the cleaning composition is suited for an end use of warewashing.

15. The composition of claim 14 further comprising an initial encapsulating coating of a cellulose derivative between the enzyme core and the first coating.

16. The composition of claim 14 further comprising, in combination with the encapsulated enzyme, a separately encapsulated chlorine bleach-neutralizing substance which comprises:
   (a) a core comprising sulf-oxy acid or salt thereof, a peroxide producing substance or a sugar; and
   (b) an encapsulating coating of a cellulose derivative.

17. The composition of claim 14 further comprising in combination with the encapsulated enzyme, a separately encapsulated diluent which comprises:
   (a) a diluent core comprising an inorganic salt;
   (b) a first encapsulating coating of a chlorine bleach-neutralizing substance comprising a sulf-oxy acid or salt thereof, a peroxide producing substance or a sugar; and
   (c) a second encapsulating coating of a cellulose derivative.

18. The composition of claim 1 wherein the sulf-oxy acid or salt thereof comprises a thiosulfite, metabisulfite, bisulfite, or salt thereof.

19. The composition of claim 14 wherein the peroxide producing substance is hydrogen peroxide, a perborate, persulfite, perphosphate, or percarbonate.

20. The composition of claim 14 wherein the polymer comprises a cellulose derivative.

21. A cleaning composition comprising:
   (a) about 0.3–20 wt-%, based upon the cleaning composition, encapsulated enzyme which comprises:
      (i) about 1 to 95 wt-%, based upon the encapsulated enzyme, enzyme core comprising a protease, a lipase, an amylase, or mixtures thereof;
      (ii) about 1–95 wt-% based upon the encapsulated enzyme, first encapsulated coating of a chlorine bleach-neutralizing substance comprising a sulf-oxy acid or salt thereof, a peroxide producing substance or a sugar; and
      (iii) about 1–50 wt-%, based upon the encapsulated enzyme, second encapsulating coating of a time-release substance comprising a cellulose derivative;
   (b) about 0.1–40 wt-% chlorine bleach; and
   (c) about 55–95 wt-%, based upon the cleaning composition, of at least one additional detergent component selected from the group consisting of detergent fillers, detergent builders, surfactants, sequestrants, and chelating agents, wherein the cleaning composition is suited for an end use of warewashing.

22. The cleaning composition of claim 21 wherein the peroxide producing substance is hydrogen peroxide, a perborate, persulfate, perphosphate, or percarbonate.

* * * * *